United States Patent [19]

Kim et al.

[11] Patent Number: 4,983,517
[45] Date of Patent: Jan. 8, 1991

[54] REACTING MATERIALS

[75] Inventors: Byung C. Kim, Columbus, Ohio; Dewey D. Y. Ryu, Davis, Calif.

[73] Assignee: Battelle Memorial Institute, Columbus, Ohio

[21] Appl. No.: 899,177

[22] Filed: Aug. 22, 1986

[51] Int. Cl.$^5$ .............................................. C12P 1/00
[52] U.S. Cl. ...................................... 435/41; 422/156
[58] Field of Search .............................. 422/139–142, 422/156; 435/68, 287, 288, 41, 174

[56] References Cited

U.S. PATENT DOCUMENTS

| | | | |
|---|---|---|---|
| 4,517,162 | 5/1985 | Moss | 422/142 |
| 4,740,216 | 4/1988 | Allard | 422/142 |

Primary Examiner—Robert A. Wax
Assistant Examiner—T. J. Wallen
Attorney, Agent, or Firm—Philip M. Dunson

[57] ABSTRACT

Methods and apparatus for reacting materials to provide a product. In a reactor (20) having an inner column (A) and an adjacent coaxial outer column (B), and having an upper zone (II) and an adjacent lower zone (I), both zones (I,II) are filled with a liquid (C). A gas (4) is fed into the liquid (C) at the lower end of the upper zone (II). The liquid (C) and a part of the gas (4) are circulated generally upward in one column (A or B) and generally downward in the other column (B or A) in the upper zone (II). Particles (15) of a solid substance are provided in a column (A or B) in the lower zone (I). The liquid (C) is circulated between the lower zone (I) and the upper zone (II) in such manner that the liquid (C) contacts and fluidizes the solid particles (15) while confining them to the lower zone (I), while the gas (4) contacts the liquid (C) and is confined to the upper zone (II).

29 Claims, 4 Drawing Sheets

REACTING MATERIALS

FIELD OF THE INVENTION

This invention relates to methods and apparatus for reacting materials, as in bioreactor systems and the like. It is especially useful for improved bioprocesses such as cultivation of animal, plant, and microbial cells; maintaining active biocatalysts such as enzymes; production of chemicals, cellular metabolites, and biologically active compounds that can be derived from cellular metabolism and/or bioconversion by enzymes; and recovery of products either simultaneously in situ or sequentially. The invention further relates to novel bioreactor designs wherein: (a) A coaxial column reactor has an inner reactor that is divided into two separate zones (or stages); (b) In the first zone (or stage) the highly active cells and/or biocatalysts are well contained and protected against shear or physical damage under very mild fluidization condition by maintaining laminar flow of only liquid phase containing nutrients, reactants, and products; and the second zone (or stage) provides supply of both gaseous and liquid form of nutrients and reactants by maintaining high turbulence and high shear mixing conditions for highly efficient mass transfer operation; (c) The mixtures of gas-liquid and/or light liquid-heavy liquid phases can be mixed and recycled through the short recycle loop consisting of shell side annulus and the ports on the inner column in the second zone (or stage); (d) The recycling flow pattern of two phase mixture in the short recycle loop in the high mass transfer zone (or stage) is achieved by the novel design of the reactor which provides ports on the inner reactor column as the reentry port and the number, size, and location of these ports are predetermined based on the fluid dynamics of two-phase flow in the airlift (i.e., draft-tube) bioreactors and other important principles involved in the optimal operation of the bioreactor system; (e) The liquid phase enriched with the nutrients and other desired solute components is recycled in the larger recycle loop consisting of the entire column length of the outer annulus space of the bioreactor and the inside space of the inner bioreactor; (f) The flow rate is controlled in such a way that the cells and/or biocatalysts are well protected from possible physical damage, when the nutrient and product-rich liquid phase flows through the growth and/or production zone (or stage) of the bioreactor; (g) The circulation rate in the short recycle loop in the high mass-transfer zone (or stage) is controlled by the gas sparging rate. The circulation rate in the larger recycle loop in the production zone (or stage) is controlled by the gas sparging rate or by the vertical distance between the gas sparger and the reentry ports; and/or (h) The bioreactor concepts combine the best features of the conventional airlift bioreactors and the conventional liquid-solid fluidized-bed bioreactors in a single bioreactor vessel.

BACKGROUND OF THE INVENTION

Biological catalysts including enzymes, bacteria, yeasts, fungi, algae, animal cells, and plant cells, have been utilized for many years to produce gene products, pharmaceuticals, biologically active compounds, biomass, primary metabolites, secondary metabolites, cellular components, proteins, etc. For such purpose, many different types of bioreactors and apparatuses have been employed to provide an adequate environment for those biocatalysts that is conducive to high productivity.

Typically such processes and apparatuses comprise mixing devices to provide good contact between biocatalysts and reactants and uniform distribution of biocatalysts, substrates, and products within the bioreactor; mass transfer devices to provide and maintain an adequate supply rate of nutrients including oxygen or carbon dioxide, substrates or reactants to the biocatalysts, provide a good mass transfer of product; and control devices to provide and maintain optimal environmental and operating conditions for the best performance of the biocatalysts and bioreactors.

For most bioreactor systems employed for microbial and enzymatic processes, standard fermenters, typically stirred tank reactor, with those devices have been satisfactorily used for many years. However, with the recent advent of biotechnology, there is an urgent need for new types of bioreactor systems specifically designed for and applicable to animal and plant cell cultures that are more delicate and sensitive to shear and other physical and chemical environmental conditions as compared to the microbial fermentation systems.

The present invention provides a novel type of bioreactor system that can be used advantageously for cultivating delicate cells like animal and plant cells and protoplasts. It also provides a novel type of bioprocess by which useful products can be made and can be recovered and/or separated simultaneously by using such a bioreactor system.

It is well recognized that several problems need to be overcome for the development of a large-scale bioreactor system and for its satisfactory operation when delicate biocatalysts are to be employed and/or cultivated. Among the critical problems to be overcome and resolved are: (A) Providing adequate mass transfer rate: Supply of oxygen and carbon dioxide to the animal and plant cells without causing any damage to the cells by high shear rate caused by the mass transfer devices and operations. (B) Removal of toxic metabolites that inhibit the growth and production of desired products especially when more than the critical amount of those toxic metabolites is accumulated in the culture medium. (C) Providing adequate strategy for the process monitoring and control based on the understanding of fundamental cellular genetic characteristics, metabolism, and physiology.

With a view to overcoming some of these critical problems in biotechnology, we have developed a novel type of bioreactor system and a set of conceptual process schemes by which it can be operated effectively to produce many different bioprocess products including gene products especially from plant and animal cells.

The present invention overcomes the major disadvantages of the prior art. It provides a significantly improved type of bioreactor system design, where sufficient mass transfer rates of nutrients including oxygen can be provided without causing any physical and/or shear damage to the biocatalysts by separating the mass transfer zone (or stage) and production zone (or stage) in a single continuous staged fluidized-bed bioreactor system. It further provides a bioprocess technology where continuous biologically catalyzed reactions are carried out over a wide range of operating conditions without losing or destroying a significant amount of biocatalysts for a prolonged operating period.

The invention provides continuous and simultaneous production and recovery of bioproducts by supplying sufficient amounts of nutrients and reactants, removing toxic metabolites continuously and recycling valuable nutrients, and selectively separating the products continuously. It also provides effective monitoring and control of important process variables for the purpose of optimal control and economic processing.

DESCRIPTION OF THE PREFERRED EMBODIMENTS

Figure 1:
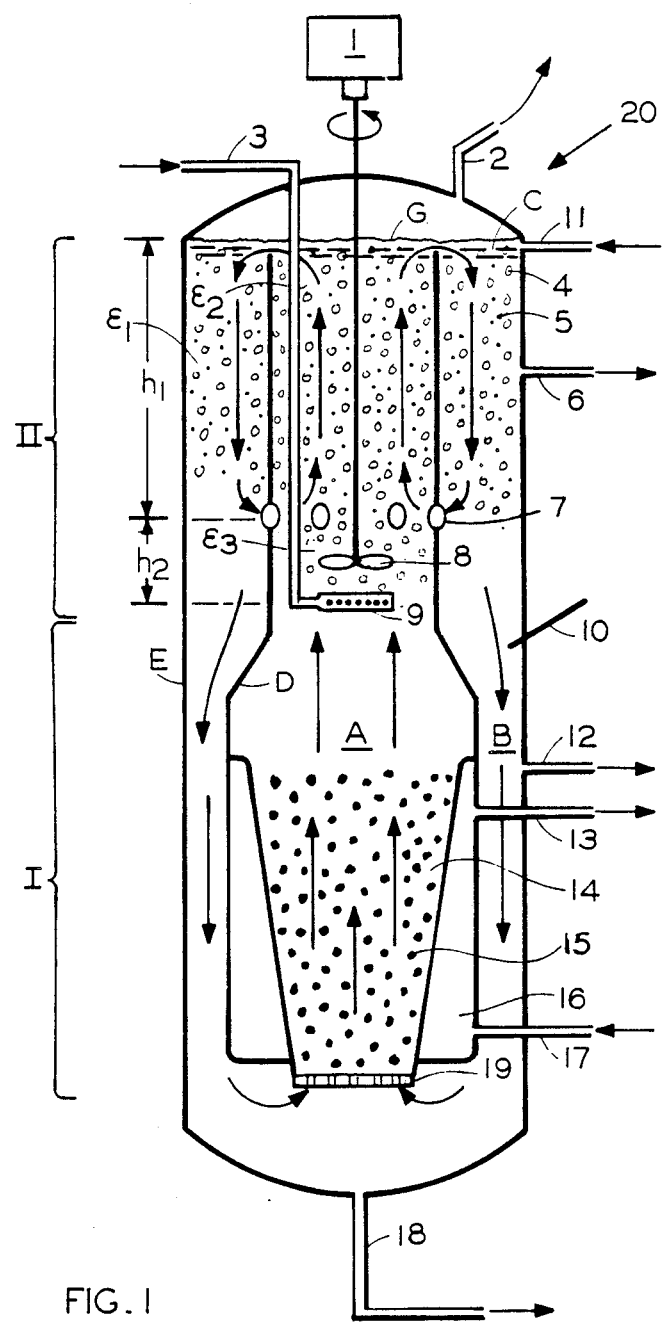
FIG. 1 is a schematic front sectional view of typical apparatus according to the present invention.
Figure 3:
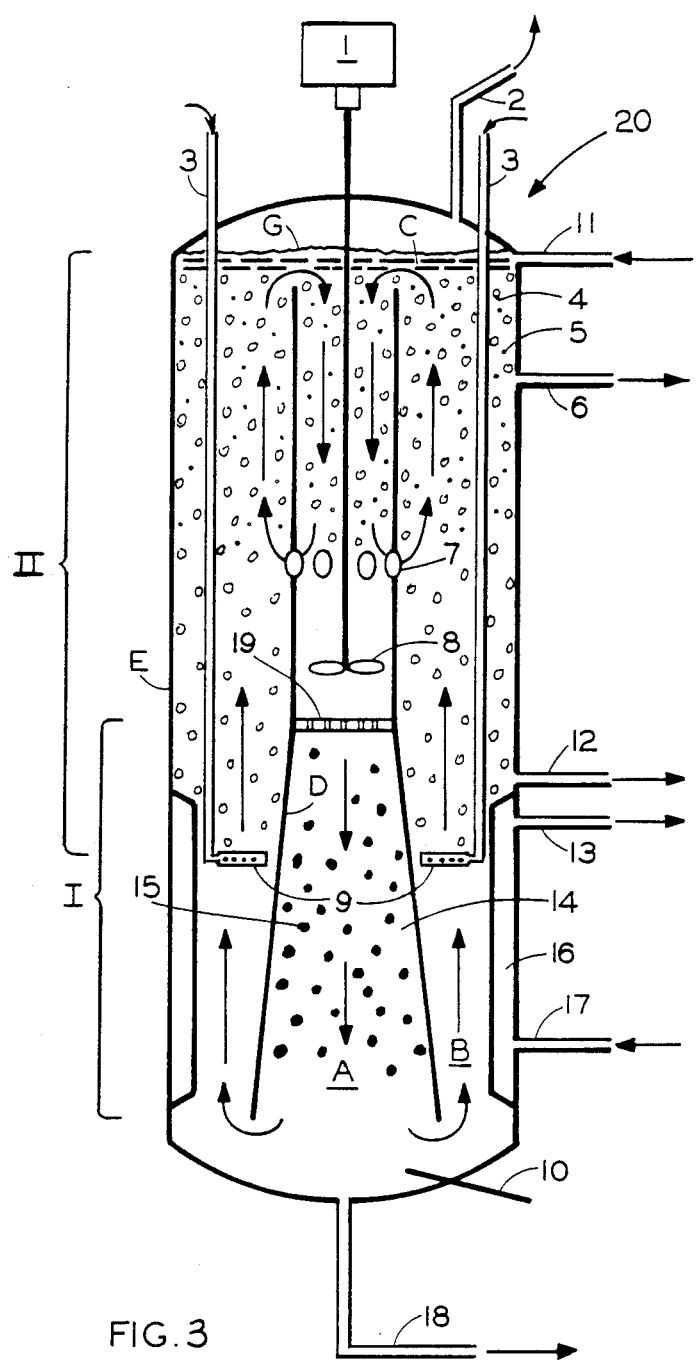
FIG. 3 is a schematic front sectional view of yet another embodiment of typical apparatus according to the present invention.
Figure 4:
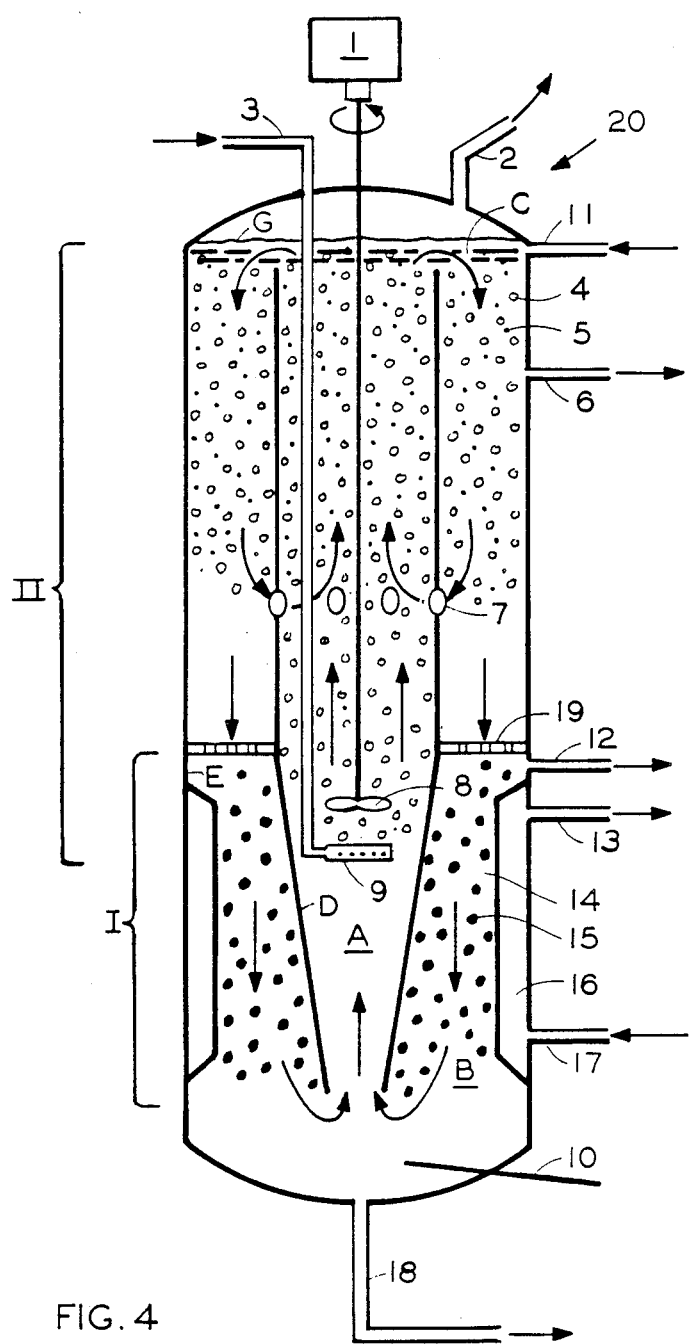
FIG. 4 is a schematic front sectional view of still another embodiment of typical apparatus according to the present invention.

A typical method according to the present invention for reacting materials to provide a product, with improved contact of gas, liquid, and solid phases in the reaction, comprises furnishing a reactor 20 having an inner column A and an adjacent coaxial outer column B, and having an upper zone II and an adjacent lower zone I; filling both zones I,II in the reactor 20 with a liquid C; feeding a gas 4 via a feed line 3 into the liquid C at the lower end of the upper zone II; circulating the liquid C and a part of the gas 4 generally upward in one column (A in FIGS. 1,4; B in FIGS. 2,3) and generally downward in the other column (B in FIGS. 1,4; A in FIGS. 2,3) in the upper zone II; providing particles 15 of a solid substance in a column (A in FIGS. 1,3; B in FIGS. 2,4) in the lower zone I; and circulating the liquid C between the lower zone I and the upper zone II in such manner that the liquid C contacts and fluidizes the solid particles 15 while confining them to the lower zone I, while the gas 4 contacts the liquid C and is confined to the upper zone II.

Typically the gas 4 expands, aerates the liquid C, and rises in the column A or B into which the gas 4 is fed. The particles 15 typically comprise catalysts, cells, enzymes, immobilized cells, and/or immobilized enzymes, of varying sizes and densities, and the liquid C typically comprises nutrients and/or reactants. Typically some of the product recirculates continuously and some of the product is removed via a line 6, 12, or 18 either continuously or intermittently. Particles 5 of an additional solid or water-immiscible liquid substance may be provided in the upper zone II and circulated in generally the same circuit as that of the liquid C and the gas 4. The particles 5 may include adsorbents, absorbents, and/or immunoadsorbents of varying physical and chemical properties.

Preferably some of the liquid C in the lower part of the upper zone II is agitated by the agitator 8 to enhance the relative movement, and thereby the rate of mass transfer, between the liquid C and the gas 4 in the upper zone II. A wall D is furnished between the inner (A) and outer (B) columns, and typically the lower part of the wall D in the upper zone II has openings 7 so that the liquid C and its contents 4,5, etc. can circulate therethrough (7) from one column A,B to the other B,A and then back over the top end of the wall D. Where (as in FIGS. 1 and 2) the solid particles 15 in the lower zone I have higher specific gravity than the liquid C therein, distributor means such as a retainer sieve plate 19 typically are furnished at the lower end of the column (A in FIG. 1; B in FIG. 2) containing the particles 15 for retaining the particles 15 therein. Where (as in FIGS. 3 and 4) the solid particles 15 in the lower zone I have lower specific gravity than the liquid C therein, distributor means such as a retainer sieve plate 15 typically are furnished at the upper end of the lower zone I in the column (A in FIG. 3; B in FIG. 4) containing the particles 15, for retaining the particles 15 in the lower zone I; and the lower end of the upper zone II, in the column not comprising the distributor means 19, may extend below the level of the distributor means 19. Heat exchange with the liquid C in the lower zone I may be provided, as by a heat exchange fluid flowing in from an inlet line 17 through a jacketed heat exchanger 16 and out via an effluent line 13, to control temperatures in the reactor 20.

The method typically comprises cultivation of animal, plant, microbial, and/or genetically engineered cells; maintaining active biocatalysts such as enzymes; production of chemicals, cellular metabolites, and/or biologically active compounds that can be derived from cellular metabolism and/or bioconversions; or recovery of products either simultaneously in situ or sequentially. Highly active and productive cells and/or biocatalysts preferably are maintained in the lower zone I of the reactor 20 by providing sufficient amounts of nutrients and reactants, while protecting them from adverse effects such as shear or physical damage by using low shear laminar flow only of liquid phase. Preferably the mass transfer zone is separated in the upper zone II of the same reactor 20 where the gaseous and liquid forms of nutrients and reactants are supplied with highly efficient mass transfer operation and significantly improved rates of mass transfer over those of the prior art. Toxic metabolites that inhibit the growth and production of desired products preferably are removed continuously, thereby overcoming the problems caused by the accumulation of toxic metabolites in conventional batch reactor systems. The method typically comprises facilitating continuous process monitoring and control, thereby achieving significant improvement of productivity and product quality. The method typically comprises continuous and simultaneous production and separation of cells, virus, vaccines, antibodies, enzymes, proteins, gene products, metabolites, cellular components, enzyme reaction products, biochemicals, pharmaceuticals, and/or fermentation products, and the like.

Figure 2:
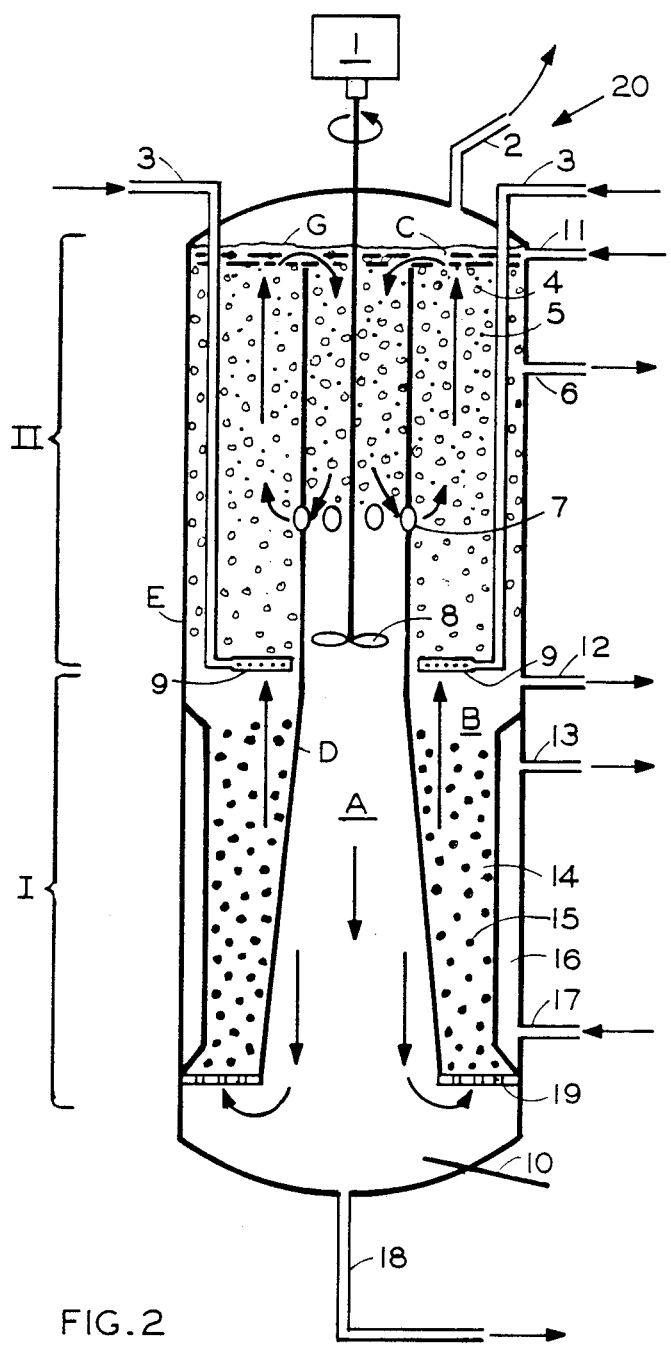
FIG. 2 is a schematic front sectional view of another embodiment of typical apparatus according to the present invention.

The mode of operation may be varied depending on the desired application; the lower zone typically contains different forms of biocatalysts, such as recombinant organisms, plant cells, animal cells, protoplasts, hybridoma cells, enzymes, virus, and/or organelles, and the like; the biocatalysts may have different preparations such as those biocatalysts adsorbed on the solid matrix, entrapped, encapsulated, aggregated, and/or freely suspended; the lower zone may be operated as either a fluidized bed or a fixed bed by controlling the flow velocity of the liquid medium relative to the minimum fluidization velocity of the biocatalyst particles; either aqueous medium or a mixture of aqueous and organic fluid may be passed through the lower zone, nutrients and/or reactants may be supplied to the biocatalysts, and products may be removed from the lower zone simultaneously; in the upper zone, different combinations of gas-liquid, light liquid-heavy liquid, gas-liquid-light solid, gas-liquid-light liquid and/or other combinations may be used for different purposes and applications; the gas phase may be enriched with pure oxygen where necessary; and/or gas, light liquid, and light solid phases may be confined within the upper zone.

Where the gas 4 is fed into the inner column A, as in FIGS. 1 and 4; the direction of the fluid circulations in both the short and the long recycle loops is downward in the outer column B and upward in the inner column A; and the biocatalyst particles 15 in the lower zone I either are placed in the inner column A (as in FIG. 1) and are fluidized by the liquid medium C flowing upward in the inner column A, or else (as in FIG. 4) the biocatalysts 15 are adsorbed or supported on a light carrier material, such as hollow glass beads, so that the specific gravity of the biocatalyst particles 15 is less than that of the liquid medium C, and the biocatalyst particles 15 are placed in the outer column B and are fluidized by the liquid medium C flowing downward therein, to obtain an inverse fluidized bed.

Where the gas 4 is fed into the outer column B, as in FIGS. 2 and 3; the direction of the fluid circulations in both the short and the long recycle loops is downward in the inner column A and upward in the outer column B; and the biocatalyst particles in the lower zone I either are placed in the outer column B (as in FIG. 2) and are fluidized by the liquid medium C flowing upward in the outer column B, or else (as in FIG. 3) the biocatalysts 15 are adsorbed or supported on a light carrier material, such as hollow glass beads, so that the specific gravity of the biocatalyst particles 15 is less than that of the liquid medium C, and the biocatalyst particles 15 are placed in the inner column A and are fluidized by the liquid medium C flowing downward therein, to obtain an inverse fluidized bed.

An inverse fluidized bed may be provided either in the inner column A, as in FIG. 3, or in the outer column B, as in FIG. 4. Typically the liquid circulation rates in the upper zone II and the lower zone I are controlled by varying the rate of feeding the gas 4 into the liquid C. Typically the liquid circulation rate in the lower zone I is controlled by varying the vertical distance between the level (9) at which the gas 4 is fed by the sparger 9 into the liquid C and the locations of the openings 7 in the wall D between the columns A and B.

Typical apparatus according to the present invention for reacting materials to provide a product, comprises reactor means 20 having an inner column A and an adjacent coaxial outer column B, and having an upper zone II and an adjacent lower zone I; means for filling both zones I,II in the reactor 20 with a liquid C; means 3,9 for feeding a gas 4 into the liquid C at the lower end of the upper zone II; means such as a motor 1 and an agitator 8 for circulating the liquid C and a part of the gas 4 generally upward in one column (A in FIGS. 1,4; B in FIGS. 2,3) and generally downward in the other column (B in FIGS. 1,4; A in FIGS. 2,3) in the upper zone II; means such as a feed line (e.g. 11 in FIGS. 1 and 2; 18 in FIGS. 3 and 4) for providing particles 15 of a solid substance in a column (A in FIGS. 1,3; B in FIGS. 2,4) in the lower zone I; and means including the agitator 8, confining walls D and E, and a retainer sieve plate 19 for circulating the liquid C between the lower zone I and the upper zone II in such manner that the liquid C contacts and fluidizes the solid particles 15 while confining them to the lower zone I, while the gas 4 contacts the liquid C and is confined to the upper zone II.

Typically the gas feeding means 3,9 comprises means 9 for sparging the gas 4, so that the gas 4 expands, aerates the liquid C, and rises in the column A or B into which the gas 4 is fed. The particles 15 typically comprise catalysts, cells, enzymes, immobilized cells, immobilized enzymes and/or other biological catalysts of varying sizes and densities, and the liquid C typically comprises nutrients and/or reactants. Typically included are means such as the wall D and the openings 7 therein for continuously recirculating some of the product and means such as the lines 6, 12, and 18 for removing some of the products either continuously or intermittently. Typically particles 5 of an additional solid or water-immiscible liquid substance are provided in the upper zone II and the gas circulating means 3,9 circulates them also in generally the same circuit as that of the liquid C and the gas 4. The particles 5 may include adsorbents, absorbents, and/or immunoadsorbents of varying physical and chemical properties. Nutrients, reactants, and particles 5 may be introduced into the reactor 20 through the line 11 either continuously or intermittently. Particles 5 loaded with product or toxic metabolites may be removed through the line 6 either continuously or intermittently.

Preferably the circulating means comprise means 8 for agitating some of the liquid C in the lower part of the upper zone II to enhance the relative movement, and thereby the rate of mass transfer, between the liquid C and the gas 4 in the upper zone II. A wall D is provided between the inner (A) and outer (B) columns of the reactor 20. Typically the lower part of the wall D in the upper zone II has openings 7 so that the liquid C and its contents 4,5, etc. can circulate therethrough (7) from one column A,B to the other B,A and then back over the top end of the wall D.

For use with solid particles 15 in the lower zone I that have higher specific gravity than the liquid C therein, the apparatus typically comprises (as in FIGS. 1 and 2) distributor means such as a retainer sieve plate 19 at the lower end of the column (A in FIG. 1; B in FIG. 2) containing the particles 15, for retaining the particles 15 therein. For use with solid particles 15 in the lower zone I that have lower specific gravity than the liquid C therein, the apparatus typically comprises (as in FIGS. 3 and 4) distributor means such as a retainer sieve plate 19 at the upper end of the lower zone I in the column (A in FIG. 3; B in FIG. A) containing the particles 15, for retaining the particles 15 in the lower zone I; and the lower end of the upper zone II, in the column (B in FIG. 3; A in FIG. 4) not comprising the distributor means 19, may extend below the level of the distributor means 19. Typically included are means such as a fluid inlet line 17, a jacketed heat exchanger 16, and a fluid outlet line 13 for exchanging heat with the liquid C in the lower zone I, to control temperatures in the reactor 20.

Referring now to FIG. 1, a tapered cylindrical inner column A having upward orientation (wider at the top end) is placed in the lower section I of the fluidized bioreactor 20, and the lower section I is joined together with the upper section II of the bioreactor 20, which is made of a cylindrical column. (The wall D extends through both sections I and II.) The resulting bioreactor A joined together by two sections I,II serves as the inner bioreactor A and it is enclosed by an outer shell E forming a coaxial cylindrical enclosure of larger diameter. The annulus B between the coaxial walls A and B serves as the space for the recycle loops. A gas sparger 9 extends into the inner column A. The sparger elevation is adjustable but always is below the elevation of the reentry ports 7.

When a gas 4 is sparged into the inner column A, the two-phase gas-liquid mixture 4,C rises in the inner column A due to lowering of the mean fluid density in the inner column A relative to the mean fluid density in the outer annulus B. To maintain continuity, fluid C is drawn in to the inner column A from the annulus B, thereby establishing circulation between the annulus B and the inner column A.

By providing reentry ports 7 on the inner wall D, two recycle loops may be established. The first recycle loop is established in the upper section II from the top surface of the aqueous phase to the reentry ports 7. The circulation rate in the upper section II is relatively high, and some gas bubbles 4 may be entrained into the annulus B and circulated with the liquid phase C. The two-phase gas-liquid flow 4,C is also highly turbulent, promotes good mixing, and serves as the mass-transfer zone. However, the highly turbulent high shear zone is localized and contained within the upper section II of the bioreactor 20. For a given reactor design, the circulation rate within the upper section II through the reentry ports 7 depends mainly on the gas sparging rate from the sparger 9.

The second recycle loop is established from the top surface of the aqueous phase to the bottom of the bioreactor 20. The liquid medium C enriched with nutrients and reactants (both gaseous and biochemical) can be circulated through the entire bioreactor 20 by flowing down through the outer annulus space B and then up through the lower section I of the inner bioreactor A under the conditions of little or no shear, and it supplies nutrients and reactants to the biocatalysts 15 and cells contained in the lower section I of the inner bioreactor A. The flow rate of the liquid medium C through the lower section I depends mainly on the gas sparging rate and also on the vertical distance between the reentry ports 7 and the gas sparger 9. Therefore, by adjusting the elevation of the gas sparger 9, the circulation rate in the lower section I can be controlled independent of the circulation rate in the upper section II of the bioreactor 20.

In each figure of the drawings, the bioreactor 20 comprises the following features and components.

The zone I or first stage is in the lower section of the bioreactor 20. Functionally, it is a growth stage or production stage. It contains biocatalysts 15, typically comprising plant or animal cells, microbial cells, recombinant cells, enzymes, organelles, or protoplasts. Biocatalyst preparation can be free suspension, immobilized, entrapped, or encapsulated cells or enzymes. The biocatalysts 15 are fluidized by the recirculating liquid phase C. The zone II or second stage is in the upper section of the bioreactor 20. Functionally, it is a mass transfer stage or separation stage. It contains gas bubbles 4 and adsorbents 5 used for separation, and/or aqueous phase C. By means of agitation, aeration and recirculation, very effective mass transfer operation takes place for oxygen, carbon dioxide, and other nutrients. The gas-liquid-solid phase mixture 4,C,5 can be recirculated in the zone II through the reentry ports 7 on the upper section of the cylindrical wall D.

An agitator motor 1 drives a pitched turbine blade type agitator 8 for mixing, mass transfer, and recirculation of the gas-liquid-solid mixture 4,C,5 in the upper section II of the bioreactor 20. The container wall E of the reactor 20 has openings through which are connected a gas exhaust line 2, a feed line 3 for gas (air, oxygen, carbon dioxide or any other gas as needed), a feed line or effluent line 6 for the product recovery as needed, a feed line 11 for adsorbents 5 and for medium containing nutrients, substrates, and reactants, a feed line or effluent line 12 for product recovery, an effluent line 13 for heat exchanger fluid from a jacketed heat exchanger 16 for control of bioreactor temperature, an inlet line 17 for the heat exchanger fluid, and a feed line or effluent line 18 for product recovery as needed.

The adsorbents 5 typically comprise light adsorbent particles or light water-immiscible organic liquid sorbents with lower specific gravity than the liquid C, which can be used for separation of products and/or toxic metabolites, including immunochemical affinity adsorbent, ion exchange resin, organic solvents, and others. In the upper portion of the inner cylindrical wall D are reentry and/or recycle ports 7 for recirculation of gas-liquid-solid phase mixtures in the bioreactor zone II. The number, size, and location of the reentry port holes 7 may be adjustable as needed depending on the process and product. The gas 4 is fed via the feed line 3 and a gas sparger 9 to the upper zone II. The tapered column bioreactor section 14 in the lower zone I includes a retainer sieve plate 19 for retaining the biocatalysts 15 therein. Probes and sensors 10 are provided for process monitoring and control, including oxygen, carbon dioxide, pH, redox potential, various ion specific probes, and biochemical specific enzyme probes.

The driving force for the circulation of the gas-liquid mixture 4,C in the upper section II containing the mass-transfer zone is provided by the difference in the hydrostatic heads in the outer annulus space B and in the inner column A between the liquid surface G and the reentry ports 7. Referring now to FIG. 1:

$$H_1 - H_2 = h_1(\rho_1 - \rho_g)(\epsilon_2 - \epsilon_1)$$

where $H_1$ = hydrostatic head in the outer annulus space B between the liquid surface G and the reentry ports 7.

$H_2$ = hydrostatic head in the inner column A between the liquid surface G and the reentry ports 7.

$h_1$ = vertical distance between the liquid surface G and the reentry ports 7.

$\rho_1$ = density of the liquid phase C.

$\rho_g$ = density of the gas phase 4.

$\epsilon_1$ = volume fraction of the gas phase 4 in the outer annulus space B between the liquid surface G and the reentry ports 7.

$\epsilon_2$ = volume fraction of the gas phase 4 in the inner column A between the liquid surface G and the reentry ports 7.

The gas sparging rate determines $\epsilon_1$ and $\epsilon_2$ and thereby controls the circulation rate. The circulation rate, therefore, may be increased or decreased by increasing or decreasing the gas sparging rate. The circulation rate also depends on the bioreactor design parameters, such as the number, size, and location of the reentry ports 7, and the diameters of the coaxial walls A and B.

The driving force for the circulation of the liquid medium C in the lower section I containing the production zone and the biocatalyst 15 is provided by the difference in the hydrostatic heads in the outer annulus space B and the inner column A between the liquid reentry ports 7 and the gas sparger 9. Again referring to FIG. 1:

$$H_3 - H_4 = h_2(\rho_1 - \rho_g)(\epsilon_3)$$

where $H_3$ = hydrostatic head in the annulus B between the reentry ports 7 and the gas sparger 9.

$H_4$ = hydrostatic head in the inner column A between the reentry ports 7 and the gas sparger 9.

$h_2$ = vertical distance between the reentry ports 7 and the gas sparger 9.

$\epsilon_3$ = volume fraction of the gas phase 4 in the inner column A between the reentry ports 7 and the gas sparger 9.

The circulation rate in the lower section can be controlled by the sparger elevation or by the gas sparging rate, which determine $h_2$ and $\epsilon_3$, respectively. The circulation rate, therefore, can be increased or decreased by increasing or decreasing the vertical distance between the reentry ports 7 and the gas sparger 9, or by increasing or decreasing the gas sparging rate.

Usually, the lower section I of the inner bioreactor A serves as the cell growth and/or production stage and the upper section II of the inner bioreactor A serves as mass transfer stage where the medium C is enriched with the nutrients.

The spent liquid medium C enriched with product completes the recycle loop by flowing through the upper section II of the inner bioreactor A where the liquid medium C is once again enriched with the nutrients and reactants in the high mass transfer zone II. This process is repeated under the well controlled process conditions.

The mass transfer rate can be enhanced if necessary by using the pitched turbine blade type agitator system 8 which can be installed just above the sparger 9. The combined action of aeration and agitation increases the shear and gas-liquid interfacial area and it results in a significantly increased mass transfer rate in this upper section II of the bioreactor 20.

The cell growth and/or production stage in the lower section I of the bioreactor 20 can be jacketed, as at 16, and the bioreactor temperature can be controlled accurately by passing the heat exchange fluid via the inlet 17 through the jacket and out via the outlet 13.

Various types of sensors and probes 10 can be inserted into the bioreactor 20 for monitoring and/or controlling the key variables. The sensors may include oxygen probe, $CO_2$ probe, pH probe, redox potential probe, and other analytical probes such as ion specific or biochemical specific enzyme probes. On-line analytical instruments can also be installed for continuous monitoring, analysis, and control of the process variables as needed.

Many variables related to the bioreactor design, operating conditions as well as biological parameters affect the performance of the bioreactor system, and each process should be optimized in terms of those key variables depending upon the cell or biocatalyst system, product, and other requirements.

The products can be recovered continuously by withdrawing a fraction of the recycling stream from the production stage and recovering the product using a separator located outside the bioreactor. An alternative mode of continuous product recovery is to use a product specific adsorbent such as an immunochemical adsorbent made of light carrier material such as a light porous resin, by recycling the adsorbent through and within the upper zone II of the bioreactor 20. A fraction of the recycle stream containing the adsorbent enriched with the product can be withdrawn for further separation and purification of product outside the bioreactor 20, and the adsorbent can be recycled back to the bioreactor 20. Instead of the solid adsorbent, a light, water-immiscible liquid sorbent such as an organic solvent may be used for the product extraction (as via the line 6) in the upper zone II of the bioreactor 20.

Partial purging of the broth or medium and continuous removal of toxic metabolites might become desirable in some cases where the toxic metabolites accumulate beyond the critical concentration level. The ratio of recycle (back to bioreactor) to purge fraction after product recovery is determined by the concentrations of toxic metabolites and the valuable nutrients such as a serum rich medium for animal cell culture.

Typical important applications of our novel bioreactor system and bioprocess include:

A. Cultivation of shear sensitive cells including animal cells, plant cells, hybridoma cells, and other recombinant cells, where in the lower zone I cells are cultivated and products harvested continuously while the upper zone II can provide a good mixing zone and sufficient amounts of nutrients and oxygen can be supplied to the cells. At the same time, toxic substances or metabolites, if any, can be removed continuously from the bioreactor.

B. Simultaneous production and separation of vaccines, monoclonal antibodies, polyclonal antibodies, enzymes, proteins, and other gene products that can be derived from the cells, where products are made in zone I and separated in zone II by extraction, adsorption, or other separation techniques in the same reactor and the product fraction is removed from the bioreactor continuously and further purified outside the reactor. Light solid particles such as adsorbent or water-immiscible organic liquid sorbent can be used when it is required for continuous separation of product and/or toxic metabolites in zone II and recycled back to the bioreactor.

C. Cultivation of anchorage dependent cells that can be anchored and/or adsorbed on the microcarrier or the equivalent particles where the cells can be adsorbed and suspended in the zone I, where cell concentration as well as the productivity can be significantly increased.

D. Cultivation of immobilized cells, either entrapped or encapsulated, and production of cellular metabolites and other products that could be derived from cells in zone I, where the immobilized cells are suspended in the zone I and the products are separated from either zone II (in the case of extracellular products) or zone I (in the case of intracellular products).

E. Reactions with immobilized enzyme systems and production of the enzyme reaction products in zone I, where immobilized enzyme particles are suspended in the zone I and enzyme reaction products are separated from the zone II.

F. Continuous chromatography (including affinity, ion-exchange, gel filtration, etc.), where the solid particles are suspended in the zone I and the product is separated by alternating the solution containing product and eluent in the feed.

G. Enhancement of gas (oxygen, carbon dioxide, and others) transfer rate by enriching air with the desired gas or by using silicone fluids or fluorinated hydrocarbons, where this enrichment can be achieved in the zone II.

H. Other applications where the desired reaction is carried out in the zone I under the optimal conditions and the product can be separated from the zone II by using appropriate separation techniques.

I. Where foaming is a problem, a light non-toxic organic phase (e.g. silicone based organic solvent having an antifoam activity) can be used in the upper section zone II to prevent severe foaming. The light organic fluid can be recirculated primarily in zone II, and can facilitate high mass transfer rate of nutrient, oxygen, and $CO_2$, and at the same time provide a driving force for laminar flow of aqueous phase throughout the reactor.

J. The mode of operation may be varied widely depending on the desired application.

The zone I (lower section of the bioreactor) may contain different forms of biocatalysts, such as recombinant microorganisms, plant cells, animal cells, protoplasts, hybridoma cells, enzymes, virus, and organelles. The biocatalysts may have different preparations such as biocatalysts adsorbed on a solid matrix, entrapped, encapsulated, aggregated, and/or freely suspended.

The zone I may be operated as either a fluidized bed or a fixed bed by controlling the flow velocity of the liquid medium relative to the minimum fluidization velocity of the biocatalyst particles.

Either aqueous medium or a mixture of aqueous and organic fluid can be passed through the zone I and supply nutrients and/or reactants to the biocatalysts and remove products from zone I simultaneously.

In the zone II (upper section of the bioreactor) different combinations of gas-liquid, light liquid-liquid, gas-liquid-light solid, gas-liquid-light liquid, may be used for different purposes. The gas phase may be enriched with pure oxygen if necessary. Gas, light liquid, and light solid phases may be contained within the upper zone recycle loop.

K. The reactor configuration also may be varied depending on the desired application.

The gas sparger 9 may be placed in the outer annulus space B, as in FIGS. 2 and 3. The direction of the fluid circulations in both the short and the long recycle loops is then reversed; the flow is downward in the inner column A and upward in the outer annulus space B. In FIG. 2 the biocatalyst particles 15 in the lower zone I are placed in the outer annulus B and are fluidized by the aqueous liquid medium C flowing upward in the outer annular space B.

The biocatalyst 15 may be adsorbed or supported on a light carrier material (e.g., hollow glass beads) so that the specific gravity of the biocatalyst particles 15 may be less than the specific gravity of the aqueous liquid medium C, and the biocatalyst particles 15 will float in the aqueous liquid medium C. The light catalyst particles 15 may be fluidized by the aqueous liquid medium C flowing downward to establish inverse fluidized beds as in FIGS. 3 and 4.

The inverse fluidized bed may be established in the inner column A as in FIG. 3 or in the outer annulus space B as in FIG. 4.

EXAMPLE 1

The following observations were made from the operation of the new bioreactor model:

a. The bioreactor bed can be fluidized in the two-phase liquid fluidized bed mode operation by recirculation of aqueous phase alone caused by the driving force generated in the mass-transfer zone I.

b. Two flow patterns were observed. A relatively high flow rate gas-liquid mixed phase in the recirculation loop between the top of the bioreactor and the reentry port holes 7 in the upper section zone II, and relatively much slower flow rate of liquid phase C only in the lower section zone I, both the downward flow through the outer annulus B and the upward flow through the bioreactor in zone I where biocatalysts are contained.

c. The fluidization test showed that the bed expansion volume depends on the gas flow rate, the liquid density the position of the sparger 9 relative to the reentry ports 7, the amount, particle size, and density of the biocatalyst particles 15 in zone I, the design geometry of the bioreactor 20, and the size, number, and location of the reentry port holes 7 in the upper zone II. The test results are shown in Table 1 below.

TABLE 1

| Vertical Distance between the sparger & reentry ports (in.) | Aeration rate (SCFM) | Fluidized-bed height (in.) | Bed expansion (in.) |
| --- | --- | --- | --- |
| 3.0 | 0. | 4.0 | 0. |
| 3.0 | 0.013 | 5.5 | 1.5 |
| 3.0 | 0.017 | 7.0 | 3.0 |
| 3.0 | 0.021 | 10.0 | 6.0 |
| 2.25 | 0.013 | 4.0 | 0.0 |
| 2.25 | 0.017 | 5.0 | 1.0 |
| 2.25 | 0.021 | 7.5 | 3.5 |

The best results demonstrated the feasibility of operating a continuous staged multiphase fluidized-bed (CSMFB) bioreactor system as the novel design had originally intended. The cell growth/production stage, zone I, and the mass transfer stage, zone II, can be separated operationally, thereby providing highly desirable conditions. Namely, the lower zone I can be operated as a fluidized bed free from damaging shear effect and the upper zone II can be operated under high shear conditions to maximize the mass transfer rate.

EXAMPLE 2

Hybridoma cells obtained from mouse spleen cells fused with Myeloma SP2/0 were cultivated in the bioreactor system and the concentrations of viable cells and the antibody produced which is active against anti-IgG2b were measured. The results of the bioreactor performance were compared with the results obtained from a conventional batch culture, as shown in Table 2 below.

TABLE 2

| Cultivation/ Bioreactor System | Viable Cell Concentration (cells/ml) | Specific rate of antibody production ($\mu g /10^6$cells/hr) |
| --- | --- | --- |
| New Bioreactor (CSMFB) (this invention) | $8 \times 10^6$ | 54.8 |
| Conventional batch culture | $5 \times 10^5$ | 1.1 |

The results indicate that the performance of the new bioreactor design (CSMFB) is far superior to the conventional batch culture system for antibody production. Approximately 50 times antibody productivity and 15 times viable cell concentration were obtained with the new bioreactor system.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. A method for reacting materials to provide a product, comprising
    furnishing a reactor having an inner column and an adjacent coaxial outer column, the reactor having throughout both columns an upper zone with an upper end and a lower end, and a lower zone with an upper end and a lower end; the lower end of the upper zone being adjacent to the upper end of the lower zone and communicating therewith in both columns;
    filling both zones in the reactor with a liquid;
    feeding a gas into the liquid at the lower end of the upper zone;
    circulating the liquid and a part of the gas generally upward in one column and generally downward in the other column in the upper zone;
    providing particles of a solid substance in a column in the lower zone; and
    circulating the liquid between the lower zone and the upper zone in such manner that the liquid contacts and fluidizes the solid particles while confining them to the lower zone, while the gas contacts the liquid and is confined to the upper zone, thereby enabling the liquid to react with the solid particles and with the gas.

2. A method as in claim 1, wherein the gas expands, aerates the liquid, and rises in the column into which the gas is fed. (No change.)

3. A method as in claim 1, wherein the particles in the lower zone comprise a material selected from the group consisting of catalysts, cells, and enzymes, of varying sizes and densities, and the liquid comprises a material selected from the group consisting of nutrients and reactants.

4. A method as in claim 1, wherein some of the product recirculates continuously and some of the product is removed continuously. (No further change.)

5. A method as in claim 1, comprising also providing particles of an additional solid substance in both columns of the upper zone and circulating them in generally the same circuit as that of the liquid and gas.

6. A method as in claim 5, wherein the particles in the upper zone include adsorbents of varying physical and chemical properties.

7. A method as in claim 5, comprising continuous and simultaneous production of antibodies, wherein the particles in the lower zone comprise cells, and the particles in the upper zone comprise adsorbents. (No change.)

8. A method as in claim 5, wherein the particles in the upper zone include absorbents of varying physical and chemical properties.

9. A method as in claim 1, comprising agitating some of the liquid in the lower part of the upper zone to enhance the relative movement, and thereby the rate of mass transfer, between the liquid and the gas in the upper zone. (No change.)

10. A method as in claim 1, wherein the axis of the coaxial columns is substantially vertical and a wall, having its top end at the upper end of the upper zone and its bottom end at the lower end of the lower zone, is furnished between the inner and outer columns, and the lower part of the wall in the upper zone has openings so that the liquid and its contents can circulate therethrough from one column to the other and then back over the top end of the wall.

11. A method as in claim 10, wherein the liquid circulation rate in the lower zone is controlled by varying the vertical distance between the level at which the gas is fed into the liquid and the locations of the openings in the wall between the columns. (No change.)

12. A method as in claim 1, wherein the solid particles in the lower zone have higher specific gravity than the liquid therein, and distributor means are furnished at the lower end of the column containing the particles for retaining the particles therein. (No change.)

13. A method as in claim 1, wherein the solid particles in the lower zone have lower specific gravity than the liquid therein, and distributor means are furnished at the upper end of the lower zone in the column containing the particles, for retaining the particles in the lower zone. (No change.)

14. A method as in claim 13, wherein the lower end of the upper zone, in the column not comprising the distributor means, extends below the level of the distributor means. (No change.)

15. A method as in claim 1, comprising also exchanging heat with the liquid in the lower zone, to control temperatures in the reactor, by conducting heat exchange fluid into, through, and away from jacketed heat exchange means in contact with the liquid in the lower zone. (No further change.)

16. A method as in claim 1, wherein highly active and productive cells are maintained in the lower zone of the reactor by providing nutrients, while protecting them from adverse physical effects by using low shear laminar flow only of liquid phase.

17. A method as in claim 1, wherein gaseous and liquid forms of nutrients and reactants are supplied to the liquid in the upper zone to provide mass transfer operation. (No further change.)

18. A method as in claim 1, wherein the solid particles comprise biocatalyst particles; the gas is fed into the inner column; the direction of the fluid circulations in both the short and the long recycle loops is downward in the outer column and upward in the inner column; and the biocatalyst particles in the lower zone either are placed in the inner column and are fluidized by the liquid medium flowing upward in the inner column, or else the biocatalysts are adsorbed or supported on a light carrier material so that the specific gravity of the biocatalyst particles is less than that of the liquid medium, and the biocatalyst particles are placed in the outer column and are fluidized by the liquid medium flowing downward therein, to obtain an inverse fluidized bed. (No further change.)

19. A method as in claim 1, wherein the solid particles comprise biocatalyst particles; the gas is fed into the outer column; the direction of the fluid circulations in both the short and the long recycle loops is downward in the inner column and upward in the outer column; and the biocatalyst particles in the lower zone either are placed in the outer column and are fluidized by the liquid medium flowing upward in the outer column, or else the biocatalysts are adsorbed or supported on a light carrier material so that the specific gravity of the biocatalyst particles is less than that of the liquid medium, and the biocatalyst particles are placed in the inner column and are fluidized by the liquid medium flowing downward therein, to obtain an inverse fluidized bed. (No further change.)

20. A method as in claim 1, wherein an inverse fluidized bed is provided in the inner column. (No further change.)

21. A method as in claim 1, wherein the liquid circulation rates in the upper zone and the lower zone are controlled by varying the rate of feeding the gas into the liquid. (No change.)

22. A method as in claim 1, wherein the particles in the lower zone comprise a material selected from the group consisting of immobilized cells and immobilized enzymes.

23. A method as in claim 1, wherein some of the product recirculates continuously and some of the product is removed intermittently. (No change.)

24. A method as in claim 1, comprising also providing particles of a water-immiscible liquid substance in the upper zone and circulating them in generally the same circuit as that of the liquid and gas. (No change.)

25. A method as in claim 5, wherein the particles in the upper zone include immunoadsorbents of varying physical and chemical properties. (No change.)

26. A method as in claim 1, wherein an inverse fluidized bed is provided in the outer column. (No change.)

27. A method as in claim 1, wherein highly active and productive cells are maintained in the lower zone of the reactor by providing reactants, while protecting them from adverse physical effects by using low shear laminar flow only of liquid phase.

28. A method as in claim 1, wherein highly active and productive biocatalysts are maintained in the lower zone of the reactor by providing nutrients, while protecting them from adverse physical effects by using low shear laminar flow only of liquid phase.

29. A method as in claim 1, wherein highly active and productive biocatalysts are maintained in the lower zone of the reactor by providing reactants, while protecting them from adverse physical effects by using low shear laminar flow only of liquid phase.

* * * * *